United States Patent [19]
Griffith et al.

[11] Patent Number: 4,757,804
[45] Date of Patent: Jul. 19, 1988

[54] DEVICE FOR ELECTROMAGNETIC TREATMENT OF LIVING TISSUE

[75] Inventors: Neil J. Griffith; Dan A. Vance, both of San Diego; Robert A. Schneider, Del Mar; Brian S. Kelleher, La Jolla; Peter A. Balnave, San Diego; Theodore B. Hill, Del Mar; Bruce C. Tostevin, San Diego, all of Calif.

[73] Assignee: LTI Biomedical, Inc., San Diego, Calif.

[21] Appl. No.: 899,674

[22] Filed: Aug. 25, 1986

[51] Int. Cl.$^4$ ............................................. A61B 17/52
[52] U.S. Cl. ..................................... 128/1.5; 128/82.1; 128/419 F
[58] Field of Search ............... 128/1.3, 1.5, 82.1, 128/419 F, 419 R; 336/205, 206, 223, 225

[56] References Cited

U.S. PATENT DOCUMENTS

| | | | |
|---|---|---|---|
| 3,102,245 | 8/1963 | Lawson, Jr. | 336/205 |
| 3,893,462 | 7/1975 | Manning | 128/421 |
| 3,915,151 | 10/1975 | Kraus | 128/1.5 |
| 4,056,097 | 11/1977 | Maass | 128/1.5 |
| 4,066,065 | 1/1978 | Kraus | 128/1.5 |
| 4,105,017 | 8/1978 | Ryaby et al. | 128/1.5 |
| 4,153,060 | 5/1979 | Korostoff et al. | 128/419 F |
| 4,266,532 | 5/1981 | Ryaby et al. | 128/1.5 |
| 4,306,564 | 12/1981 | Kraus | 128/419 F |
| 4,315,503 | 2/1982 | Ryaby et al. | 128/1.5 |
| 4,424,030 | 1/1984 | Smiley et al. | 433/18 |
| 4,432,361 | 2/1984 | Christensen et al. | 128/419 |
| 4,456,001 | 6/1984 | Pescatore | 128/1.5 |
| 4,467,808 | 8/1984 | Brighton | 128/419 |
| 4,467,809 | 8/1984 | Brighton | 128/419 |
| 4,501,265 | 2/1985 | Pescatore | 128/1.5 |
| 4,526,539 | 7/1985 | Blechman et al. | 433/18 |
| 4,548,208 | 10/1985 | Niemi | 128/419 |
| 4,550,714 | 11/1985 | Talish et al. | 128/1.5 |
| 4,556,051 | 12/1985 | Maurer | 128/1.5 |
| 4,561,426 | 12/1985 | Stewart | 128/1.5 |
| 4,574,809 | 3/1986 | Talish et al. | 128/419 F |
| 4,587,956 | 5/1986 | Griffin et al. | 128/1.3 |

FOREIGN PATENT DOCUMENTS 875240 7/1949 Fed. Rep. of Germany ...... 336/223

OTHER PUBLICATIONS

"Fracture Healing in the Rabbit Fibula When Subjected to Various Capacitively Coupled Electrical Fields" by Brighton et al, Journal of Orthopedic Research, vol. 3, No. 3, 1985.
"Electrical Stimulation of Hard and Soft Tissues in Animal Models" by Jonathan Black, Ph.D., *Clinics in Plastic Surgery*, vol. 12, No. 2, Apr. 1985.
"Bioelectric Stimulation of Bone Formation: Methods, Models, and Mechanisms" by Spadaro, *Journal of Bioelectricity*, vol. 1, No. 1, 1982.
"A Review of Electromagnetically Enhanced Soft Tissue Healing" by Cyril B. Frank, M.D. and Andrew Y. J. Szeto, Ph.D.
"Treatment of Osteonecrosis of the Hip with Specific, Pulsed Electromagnetic Fields (PEMFs): A Preliminary Clinical Report" by C. A. L. Bassett et al, *Journal of Bone Circulation*.

Primary Examiner—Edward M. Coven
Assistant Examiner—J. P. Lacyk
Attorney, Agent, or Firm—Brown, Martin, Haller & Meador

[57] ABSTRACT

A solenoid device for treatment of body tissue such as bones or other regions with pulsed signals comprises a flexible flat belt for encircling a body part or cast surrounding a body part containing tissue to be treated. The belt has a plurality of parallel conductors extending along its length and has its opposite ends offset by one or more conductor spacings. The resultant aligned conductor ends are connected together to form at least one continuous coil, with the resultant unconnected outer conductor ends at opposite sides of the belt comprising inputs across which a suitable electrical signal can be connected. An adjustment device or buckle is mounted on the belt to allow the diameter of the belt to be adjusted. The buckle traps a doubled over portion of the belt circumference which is adjustable in length to change the diameter of the device to closely fit the underlying body part or cast.

23 Claims, 2 Drawing Sheets

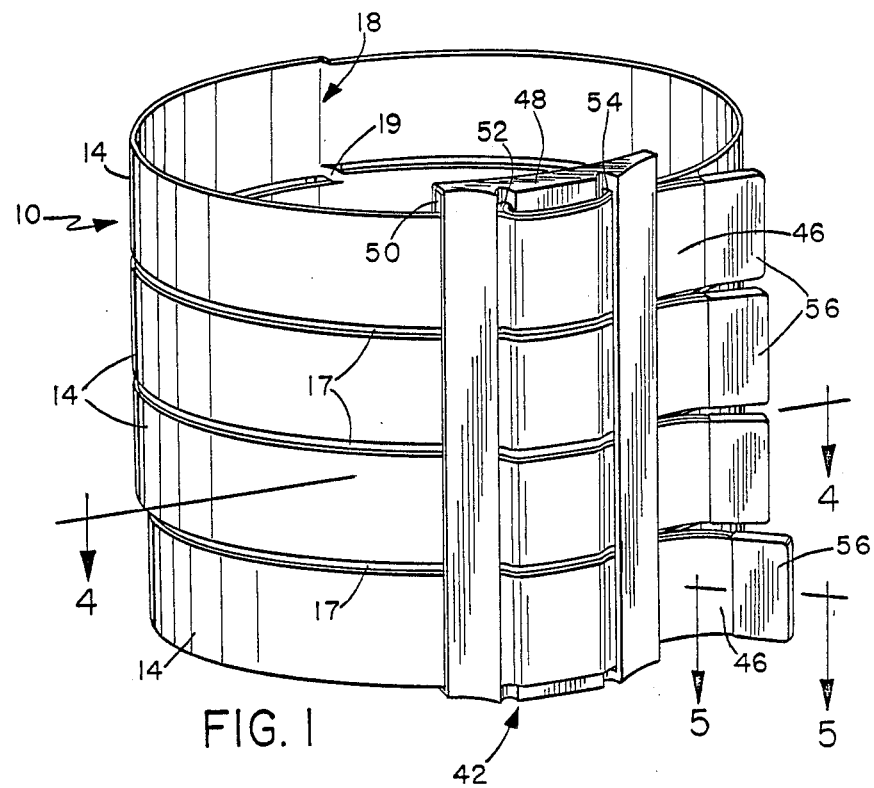
FIG. 1
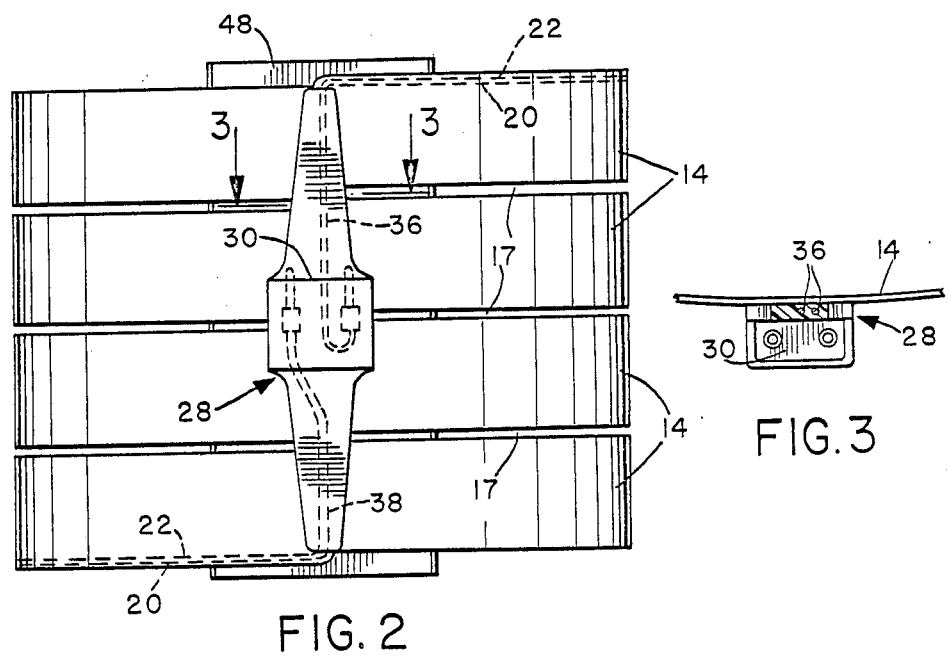
FIG. 2
FIG. 3

DEVICE FOR ELECTROMAGNETIC TREATMENT OF LIVING TISSUE

BACKGROUND OF THE INVENTION

The present invention relates to devices used in electromagnetic treatment of living tissue such as bone. It has been known for some time that certain electrical and magnetic signals can have a therapeutic effect in treatment of living tissue, and such treatment is generally known as electro-osteogenesis.

The use of electrical and electromagnetic signals in stimulating repair and growth of living tissue such as bones has been known for some time in both humans and animals. In one technique of this type electrodes are actually implanted in the tissue to be treated. An alternative technique involves the application of an electromagnetic field to the affected area via an external device such as a coil or solenoid which is secured to the body part or to a plaster cast surrounding the affected body part. The latter technique is normally more suitable since it does not require surgical invasion of the treatment site.

The problems involved in use of an external device are in accurately positioning it at a body site adjacent the internal tissue area to be treated, securing it in place so that it is reasonably comfortable and unlikely to become dislodged while allowing the subject undergoing treatment to move relatively freely, and ensuring that the required uniform field is produced. Up to now such placement has normally been done in a doctor's office or surgery, with the subject sometimes being required to stay relatively immobile while treatment is in progress.

U.S. Pat. No. 3,915,151 of Kraus shows one technique in which a coil is provided in a tubular member which can be slid over an extremity such as a leg. The coil is of rigid construction and will therefore not conform to the external shape of the leg.

The problem with encircling a body part such as an arm, leg, or torso with a rigid solenoid coil device is that the device must be large enough to slip over a relatively larger diameter body part, e.g. a hand, foot or head and shoulders, in which case it will be significantly larger than the body part it encircles when it arrives at the correct site. This results in a power consumption which is significantly larger than necessary, because the rigid construction of the coil requires that it be larger in diameter than that of the underlying body part, and the power required is proportional to $d^3$ where d represents the diameter of a basic air-core coil, e.g. a ring, solenoid, Helmholtz or similar coils.

SUMMARY OF THE INVENTION

It is an object of the present invention to provide a solenoid type treatment device which is more readily adjustable and has lower power consumption.

According to the present invention a solenoid type treatment device for application of electromagnetic signals to living tissue is in the form of a conformable coil for encircling a body part or cast covering a body part containing the treatment site. The coil is preferably belt-like and comprises a flexible tubular assembly having one or more continuous conductive coils extending along its length. The belt is preferably formed from at least one flat, flexible band or cable having a plurality of spaced parallel conductors extending along its length with opposite ends of the band offset by at least one conductor spacing and connected together by a suitable connector device which connects the aligned offset conductor ends together to form at least one continuous coil. An input device is provided for connecting a suitable pulsed electrical signal across the opposite ends of the coil, which comprise the outermost offset conductor ends projecting at opposite side edges of the belt.

An adjustment device is preferably provided to allow the diameter of the coil to be varied so that it can be fitted around body parts of different diameters, and slid over larger size extremities to reach the body region to be treated before being adjusted to a smaller diameter to fit around the body region at the treatment site. This allows for complete mobility of the patient during use. The adjustment device comprises a buckle-like device for doubling over a section of the coil circumference to form a folded portion of adjustable length and releasably securing the folded portion in place. The overlapped portion is magnetically cancelling and does not affect the induced magnetic field appreciably.

In a preferred embodiment of the invention the belt is longitudinally slit to form several separate belt sections, with each section being independently adjustable in diameter. With this arrangement the diameter of each belt section can be independently tightened around the underlying body part by the buckle-like adjustment device, so that the belt can be fitted closely to a varying diameter or tapering limb or body part. Thus the solenoid belt can be fitted to conform with the body part it encircles, making it relatively secure and unlikely to be dislodged by movement of the subject. This allows the device to be used outside doctor's offices. The device is relatively compact, easy to use, and relatively comfortable to wear. If any of the belt sections loosen, they can easily be retightened by the wearer.

In one arrangement, the offset conductor ends are permanently connected together. In another arrangement, the conductor ends are releasably secured together by suitable mateable connector pieces at respective opposite ends of the belt. This allows the belt to be placed directly around a body part or cast before connecting the belt ends and adjusting the diameter for close conformity to the underlying region, and avoids having to slide the belt over an extremity such as a foot or hand. The length of the folded portion of the belt can be significantly shorter in this case, reducing power consumption.

The belt may be made from one or more lengths of ribbon-flex type cable commonly used in the computer industry. The opposite ends of the cable are juxtaposed with the conductors offset by at least one, and the aligned conductor ends connected together to form at least one continuous coil.

BRIEF DESCRIPTION OF THE DRAWINGS

The present invention will be better understood from the following detailed description of a preferred embodiment of the invention, taken in conjunction with the accompanying drawings in which like reference numerals refer to like parts and in which:

FIG. 1 is a perspective view of an electromagnetic treatment device according to a preferred embodiment of the present invention;

FIG. 2 is a rear elevational view of the device shown in FIG. 1;

FIG. 3 is a sectional view on line 3—3 of FIG. 2;

DESCRIPTION OF THE PREFERRED EMBODIMENT

Figure 8:
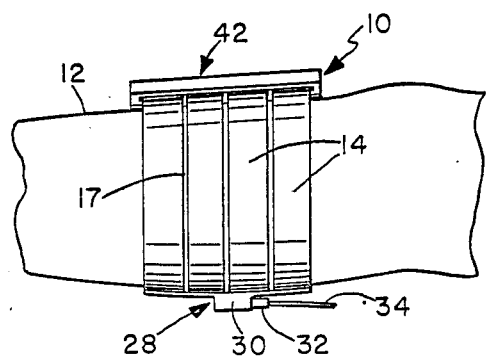
FIG. 8 is a side elevation view showing the device in use.

As shown in the drawings, a device for electromagnetic treatment of living tissue according to a preferred embodiment of the invention comprises a belt-like or tubular assembly or coil device 10 for encircling a body part or cast surrounding a body part in which the treatment area, such as a bone, is located. The device may be used in electromagnetic treatment of broken or diseased bones, for example, where such treatment has been known to encourage or promote healing, growth or repair, or in the treatment of living tissue other than bone. One example of a typical use of the device is shown in FIG. 8 of the drawings, where the device is secured around the leg 12 of a patient. Clearly the device could alternatively be secured at any chosen region of the arm, leg, head or torso of a subject, and may be used in treatment of human or animal subjects. The device may be installed around the outside of a plaster cast, wrapped in a final cast wrap, or installed directly against the body surface if comfort and edema prevention is sufficient.

Figure 6:
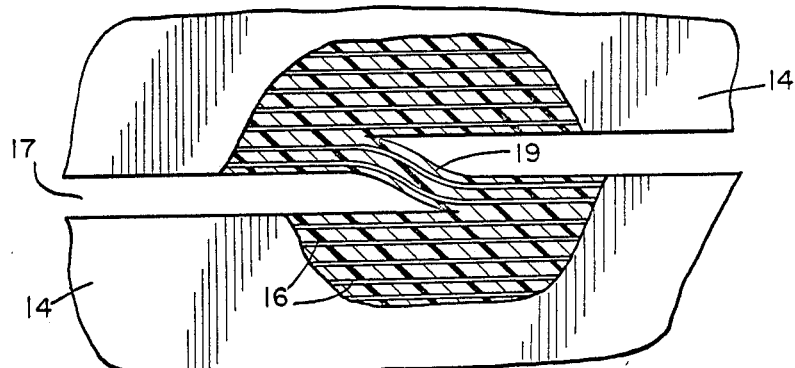
FIG. 6 is an enlarged view, partially cut away, of a coil conductor cross over between two adjacent belt sections.

As best seen in FIGS. 1 and 6, the device is formed from a number of separate flexible, flat belt sections or bands 14 each having a plurality of spaced, parallel conductor wires 16 extending along its length. The bands are preferably formed from one or more lengths of ribbon flex type cable commonly used in the computer industry, which comprises a plurality of conductor wires enclosed in suitable insulating material and bonded together to form a substantially flat, flexible band or strip. The belt sections may be formed from a single length of such cable having several longitudinal slits 17 to form the separate sections or bands, or from two or more lengths of cable placed side by side, with or without longitudinal slits to form extra bands. Although in the drawings the device is shown formed with four separate bands, a greater or lesser number of bands or belt sections may be provided.

Opposite ends of each band are placed in juxtaposition and offset by an equal number of conductor spacings before being secured together at 18 by any suitable means, for example by bonding or fusion. The resultant aligned conductor ends are electrically connected together when the belt ends are connected by any suitable means, for example by soldering, fusing or otherwise bonding the ends as generally indicated in FIG. 6. At the crossover point 19 between adjacent bands, illustrated in FIG. 6, the outer conductor ends of one band are connected to the respective outer conductor ends of the adjacent band so that one or more continuous coils are formed which extend along the length of the device 10.

Figure 7:
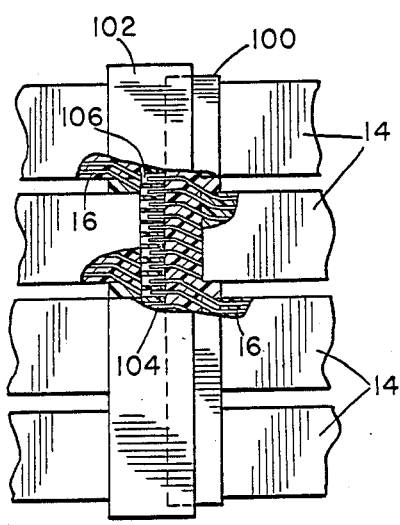
FIG. 7 is a partial rear elevational view, similar to FIG. 2, partly cut away and showing a modified separable connector device for separably connecting the belt ends.

In an alternative embodiment shown in FIG. 7, the belt ends may each be secured to mateable connector pieces 100, 102 incorporating pin and socket, insulation displacement or other types of connectors for the offset conductor ends. This allows opposite ends of the belt to be separated for removal or fitting of the belt directly around a body part or cast. In one arrangement, the conductors at one end of the belt are suitably connected to respective pins 104 of connector piece 100 while the conductors at the opposite end are connected to sockets 106 at connector piece 102 at the desired offset. Once the belt has been adjusted around a body part or cast, the pins may be soldered to the sockets by current pulse or heat wand bonding with low temperature solder. This restricts the patient from separating the belt. Alternatively, the opposite conductor ends may, for example, be received in a circuit board etched to stagger the connections between conductor ends to create one or more continuous coils.

In the illustrated embodiment, the belt is preferably formed from ribbon flex cable of the type used in the computer industry. This cable normally has a fixed number of conductors extending along its length, say N. The required number of turns can be controlled by suitable choice of the conductor end offset, or by connecting two or more separate lengths of cable side by side, for example. If a single length of N-wire ribbon flex cable has its opposite ends offset by one and the resultant aligned connector ends are suitably connected together, an N-turn solenoid is formed. If the conductor ends are offset by two, as indicated in FIG. 6, and connected together, one N/2 turn double wire solenoid is formed when the resultant outermost two unconnected conductor ends 20, 22 (see FIG. 2) at each peripheral edge of the cable are connected together. Similarly, the conductor ends may be offset by 3, 4 or more to further reduce the number of turns.

An input connector device 28 is suitably connected across the opposite ends of the resultant coil for connecting the coil to a suitable signal source (not shown) which connects an electrical signal of chosen form and strength across the coil.

The input voltage or signal strength is chosen according to the desired uniform field across the treatment area, which will be dependent on the number of turns, resistance, applied voltage and current, time constant, and the coil diameter. These parameters can be varied while still maintaining a uniform field. For example, the resistance and consequently the power can be reduced by reducing the number of turns, or by using thicker gauge wire. By allowing either single or multiple wire offsets and resultant single or multi-parallel connection of the wire ends, to produce a single or multi-wier coil, the adjustability of the device is increased and the sensitivity of the device and battery lifetime can be varied while still maintaining the required uniform field over the length of the solenoid.

Reliability of the device is also improved by offsetting the conductor ends by more than one and connecting the multiple free ends at each end of the coil together. In this case, if a single wire should break or a connection comes loose, there will still be at least one continuous coil remaining in the circuit. In a single wire coil, a single breakage results in a complete loss of signal.

The multiple wire offset also permits a smaller gauge wire to be used while still having the desired reduced number of turns. In N-wire ribbon flex cable, cable with fewer wires is normally lower gauge and thus less flexible. By using cable having more wires than the required number of turns and offsetting the conductor ends by more than one, the desired flexibility of the belt for conforming to the underlying body part or cast can be maintained.

The connector device 28 shown in FIG. 2 may, for example, comprise a standard 2 pin socket 30 or equivalent connector, as shown in FIGS. 2 and 3 of the drawings, for connection to a corresponding plug connector 32 (see FIG. 8) connected via cable 34 to the signal source. The pins of socket 30 are connected via connecting wires 36, 38 to the respective opposite ends 20, 22 of each or the coil, as shown in FIG. 2.

In one particular example, the device was formed from ribbon flex cable separated every 16 or 17 conductors to form the separate belt sections or bands to improve conformability to an underlying body part. In another example, the device was made from two 50 conductor ribbon flex cables. Clearly various other alternative constructions are possible with any chosen number of solenoids and solenoid turns. The overall solenoid length to diameter ratio may be in the range of 0.5 to 5.0, and in one example is approximately 1.0.

Figure 4:
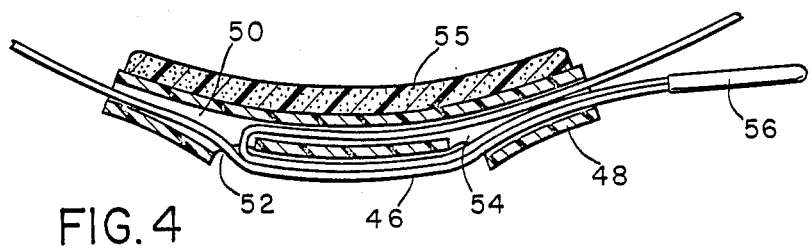
FIG. 4 is an enlarged sectional view taken on line 4—4 of FIG. 1.
Figure 5:
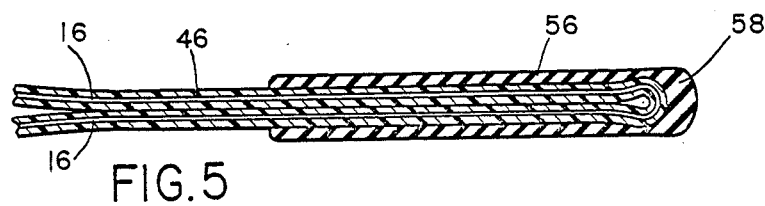
FIG. 5 is an enlarged sectional view taken on line 5—5 of FIG. 1.

As best shown in FIGS. 1 and 4, an adjustment device 42 is provided on the treatment device for allowing the treatment coil or solenoid to be adjusted in diameter. This allows the device to be adjusted to conform relatively closely to any underlying body part diameter, or to the outer diameter of a cast or other wrapping covering a body part, as described in more detail below.

The adjustment device allows each belt to be doubled over to form an overlapped folded portion 46 of adjustable length, as shown in FIG. 4. It has been found that the folded portion of the coil which results is substantially self-cancelling magnetically and thus has a minimal effect on the magnetic field geometry.

In the preferred embodiment of the invention shown in the drawings the adjustment device comprises an elongate clamping or buckle-like member 48 having a transverse through bore or channel 50 extending along its length which is slid over each of the belt sections 14. The member 48 is of relatively thin plastic and is dimensioned to be as flexible as possible for conformity with underlying body regions or cast material.

The member 48 has a first longitudinal opening 52 in its outer face communicating with the channel 50 through which the folded over portion of each belt section is pulled to adjust the diameter of that section. A second opening 54 in the outer face spaced from the first opening defines a clamping or trapping device for securing the folded over portion in place in the manner of a belt buckle once the diameter has been adjusted. The folded over portion of each belt is pulled back through this opening into the channel, and out of one end of the channel to tighten and trap the folded over portion in place.

The member 48 may be of plastics or other material and is slightly curved as shown in FIG. 4 so that it will conform relatively closely to an underlying curved body surface. The member preferably has a cushioning pad 55 of foam material or the like secured to its inner face when it is for securing directly to an affected body part. The pad contacts the underlying body surface when the device 10 is fitted to cushion the wearer from the adjustment member for added comfort.

In an alternative embodiment of the invention, the adjustment device may simply comprise a trap having an opening for trapping and pulling through the folded portion of each belt section, with the belt having releasable, mating surface regions for securing the folded portion of the belt to the underlying belt surface. The mateable surface regions may comprise strips of mateable hook and loop material for example, such as Velcro (Registered Trade Mark) strips bonded to the inner surface of each folded portion and the underlying outer belt surface.

To make the belt adjustment easier the outer end 56 of each folded portion is flattened with the opening belt surfaces secured together and capped with a flattened outer cover 58 such as a coating of rubber sealant material. This makes it easier for the folded portions to be pulled through the openings to tighten or loosen the belt section. The user simply grips the member 48 with one hand while pulling the end 56 of the respective folded portion with the other hand to pull it through the opening 52 until the belt section conforms substantially to the diameter of the underlying limb, other body part or a cast or other protective wrapping covering an injured body part.

The adjustment device is shown in the drawings as being positioned diametrically opposite the belt end connection. However it may be positioned anywhere around the periphery of the device as long as it does not interfere with the input connection. Alternatively the connection between opposite ends of the belt sections may be provided at the fold itself, reducing complexity slightly.

Although the buckle-like adjustment device 48 is shown in the drawings for adjusting the diameter of a flat belt-like solenoid preferably formed of ribbon-flex cable, it may alternatively be used for diameter adjustment of any coil encircling a cast or body part in an equivalent manner. A doubled over or folded portion is formed in the coil circumference and adjustably trapped in the device 48, in the manner indicated FIG. 4.

The signal source is suitably provided in a portable battery pack unit which can easily be carried by the subject for example in a waist band or pocket.

It can be seen from the drawings that the device can be easily installed around a body part or a cast over a body part in which an area of tissue to be treated is located, by loosening each of the bands or belt sections 14 until the overall diameter of the device is sufficient to allow it to be easily pulled over the extremity of that body part, e.g. a foot, hand or head and shoulders. Where the belt ends are separable, as in FIG. 7, the device is simply wrapped around the appropriate region before connecting the belt ends together. Once the correct region is reached, the bands can be tightened individually around the underlying body region by pulling the folded portion of each band through the first opening of the adjustment device until that band is relatively tight, and then pulling the folded portion out through the second opening to trap the folded portion in place and prevent or limit loosening.

Thus, as indicated in FIG. 7, the belt device can be adjusted to conform closely to a cylindrical body part of varying diameter, such as the tapering calf portion of a leg, for example. The device can be quickly and easily positioned and tightened over any selected body region, or a cast covering such a region including the head, neck, arms, legs or torso of a human or animal subject, and allows a wide range of diameter variation to allow for opposite extremes in limb or other body part sizes.

The device is of simple construction, is lightweight and, when used in non-cast treatments, allows more or less normal freedom of movement of the subject during use without significant loosening. If loosening should occur, the device can be quickly and easily retightened by the user. The device can be fitted and used by the subject at home when used without a cast or extra-cast, and the subject does not need to visit the doctor's office for either fitting or treatment once the procedure has been explained. The arrangement allows a sufficient solenoid turn density to be achieved while still conforming easily to the shape of the underlying body part.

The adjustment device and input connector are preferably of relativley flexible molded plastics material.

Although the device is described in the preferred embodiment as being formed by offsetting and connecting the offset ends of spaced parallel conductors contained in one or more flexible bands or cables, it may alternatively be formed by spirally wrapping one or more conductors to form a tubular assembly. The conductors may be embedded or secured in a flexible band or strip, such as a ribbon-flex cable as described above, which is then spirally wrapped and connected to a suitable input device. Alternatively the conductor forming the coil may comprise a spring which must be expanded to fit around a body part to be treated and will therefore shrink to conform to the dimensions of the body part when released.

Although a preferred embodiment of the invention has been described above by way of example only, it will be understood by those skilled in the field that modifications may be made to the disclosed embodiment without departing from the scope of the invention, which is defined by the appended claims.

We claim:

1. A device for electromagnetic treatment of living tissue, comprising:
   belt means for encircling a region containing living tissue to be treated;
   the belt means comprising at least one flexible flat belt having a plurality of conductors extending along its length, connector means for connecting opposite ends of the belt together with the ends offset by at least one conductor spacing, the connector means comprising means for electrically connecting the resultant offset aligned conductor ends together to form at least one continuous coil; and
   input means for connecting a selected pulsed electrical signal across the coil.

2. The device as claimed in claim 1, including adjustment means for adjusting the diameter of the belt.

3. The device as claimed in claim 2, wherein the adjustment means comprises foldover means for forming an overlap fold of adjustable length in the belt.

4. The device as claimed in claim 3, wherein the foldover means comprises a tightener member having a first opening through which a folded over portion of the belt projects, and fastener means for releasably securing the projecting folded portion in place.

5. The device as claimed in claim 4, wherein the tightener member has a further opening spaced from the first opening for receiving the end of the projecting folded portion, the further opening comprising said fastener means.

6. The device as claimed in claim 4, wherein the fastener means comprises releasable mating formations provided on opposing surfaces of the belt.

7. The device as claimed in claim 6, wherein the mateable formations comprise hook and loop type formations.

8. The device as claimed in claim 5, wherein the tightener member has a through bore for sliding over the belt, the openings communicating with the through bore and comprising means allowing a folded over portion of the belt to be pulled through the first opening out of the bore and pulled back through the further opening into the bore to secure the folded portion in place.

9. The device as claimed in claim 8, wherein the tightener member has a cushioned backing pad for engaging a body part encircled by the belt.

10. The device as claimed in claim 3, including cap means sealed over the end of the folded portion of the belt.

11. The device as claimed in claim 1, in which the belt means comprises a plurality of separate flexible belt sections arranged side by side and each having a plurality of conductors extending along its length, the connector means comprising means for connecting opposite ends of each belt section together with the ends offset by at least one connector spacing, means for electrically connecting the resultant aligned conductor ends in each belt section, and means for connecting the remaining outer conductor ends in adjacent belt sections together to form at least one continuous coil extending along the length of the device, the input means comprising means for connecting an input signal across the outer conductors of the outermost two belt sections.

12. The device as claimed in claim 11, wherein the belt sections are formed from a single length of flexible flat cable having a plurality of transversely spaced longitudinal splits to separate the belt sections.

13. The device as claimed in claim 11, including adjustment means for separately adjusting the diameter of each belt section to form encircling belt means having a diameter variable along its length.

14. The device as claimed in claim 13, wherein the adjustment means comprises foldover means for forming an adjustable length overlap folded portion in each belt section.

15. The device as claimed in claim 14, wherein the foldover means comprises a tightener member having a through bore through which each belt section extends, the member having a first opening communicating with the through bore for pulling the overlapped folded portion of each belt section through the opening out of the bore, and fastener means for securing the folded portion in place.

16. The device as claimed in claim 1, wherein the belt has N conductors and the opposite ends of the belt are offset by e conductor spacings where e is greater than one, the connector means comprising means for connecting the resultant aligned conductor ends together and the input means comprising means for connecting a chosen electrical signal across the outer most free conductor ends at each end of the coil to form a multi-wire N/e turn coil.

17. The device as claimed in claim 16, wherein the opposite ends of the belt are offset by two conductor spacings and the connector means comprises means for connecting the resultant aligned conductor ends together to form an N/2 coil.

18. A device for electromagnetic treatment of living tissue, comprising:

belt means for encircling a region containing living tissue to be treated;

the belt means comprising at least one flexible flat belt having a plurality of conductors extending along its length wherein the belt comprises a length of ribbon flex cable, connector means for connecting opposite ends of the belt together with the ends offset by at least one conductor spacing, the connector means comprising means for electrically connecting the resultant offset aligned conductor ends together to form at least one continuous coil; and input means for connecting a selected pulsed electrical signal across the coil.

19. The device as claimed in claim 18, wherein the belt has a plurality of transversely spaced longitudinal slits to form several separate belt sections.

20. A device for electromagnetic treatment of living tissue, comprising;

belt means for encircling a region containing living tissue to be treated;

the belt means comprises a plurality of lengths of flexible flat ribbon flex cable arranged side by side, each cable having a plurality of conductors extending along its length, connector means for connecting opposite ends of each cable together with the ends offset by at least one conductor spacing, the connector means comprising means for electrically connecting the resultant offset aligned conductor ends together to form at least one continuous coil and the connector means including means for connecting the outermost conductor ends of one of the lengths of cable to the corresponding opposite conductor ends of an adjacent length of cable; and input means for connecting a selected pulsed electrical signal across the coil.

21. A device for electromagnetic treatment of living tissue, comprising:

belt means for encircling a body part containing living tissue to be treated;

the belt means comprising a flexible flat belt having a plurality of parallel spaced conductors extending along its length, connector means for releasably connecting opposite ends of the belt together with the ends offset by at least one conductor spacing, including means for connecting the resultant aligned conductor ends together to form at least one continuous coil;

input means for connecting a selected pulsed electrical signal across the opposite ends of the coil; and adjustment means for varying the diameter of the belt means, the belt comprising several separate belt sections arranged side by side, and the adjustment means comprising means for separately adjusting the length of each belt section to form a conformable belt means having a diameter variable along its length.

22. A device for electromagnetic treatment of living tissue, comprising:

a flexible solenoid coil assembly for encircling a region containing tissue to be treated;

input means for connecting a selected electrical signal across opposite ends of the coil; and adjustment means for adjusting the diameter of the tubular member to fit an encircled body part, the adjustment means comprises means for forming a doubled back fold portion of adjustable length in the periphery of the coil assembly.

23. The device as claimed in claim 22, wherein the coil assembly comprises at least one flexible band having spaced parallel conductors extending along its length and wrapped into a spiral configuration to form a tube.

* * * * *